(12) United States Patent
Perring et al.

(10) Patent No.: US 10,722,607 B2
(45) Date of Patent: *Jul. 28, 2020

(54) PERFUME COMPOSITIONS

(71) Applicant: Givaudan SA, Vernier (CH)

(72) Inventors: Keith Douglas Perring, Ashford (GB); Michael Gordon Evans, Canterbury (GB); Alan Forbes Provan, Ashford (GB); David Jonathan Bradshaw, Ashford (GB); John Martin Behan, Ashford (GB)

(73) Assignee: GIVAUDAN S.A., Vernier (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/658,871

(22) Filed: Mar. 16, 2015

(65) Prior Publication Data

US 2015/0182656 A1    Jul. 2, 2015

Related U.S. Application Data

(60) Division of application No. 13/651,958, filed on Oct. 15, 2012, now Pat. No. 9,011,829, which is a continuation of application No. 12/375,756, filed as application No. PCT/GB2007/002980 on Aug. 3, 2007, now abandoned.

(30) Foreign Application Priority Data

Aug. 5, 2006 (GB) .................................. 0615583.2

(51) Int. Cl.
| | | |
|---|---|---|
| A61L 15/20 | (2006.01) |
| A61L 15/46 | (2006.01) |
| C11B 9/00 | (2006.01) |
| A01K 1/015 | (2006.01) |
| A61L 9/01 | (2006.01) |

(52) U.S. Cl.
CPC ............ *A61L 15/20* (2013.01); *A01K 1/0152* (2013.01); *A61L 9/01* (2013.01); *A61L 15/46* (2013.01); *C11B 9/003* (2013.01); *C11B 9/0015* (2013.01); *C11B 9/0019* (2013.01); *C11B 9/0034* (2013.01); *C11B 9/0038* (2013.01); *C11B 9/0061* (2013.01); *C11B 9/0076* (2013.01); *C11B 9/0084* (2013.01); *C11B 9/0088* (2013.01); *A61L 2300/216* (2013.01)

(58) Field of Classification Search
None
See application file for complete search history.

(56) References Cited

U.S. PATENT DOCUMENTS

| | | |
|---|---|---|
| 588,961 A | 8/1897 | Dement |
| 3,185,629 A | 5/1965 | Beets et al. |
| 3,945,950 A | 3/1976 | Vosganiantz |
| 4,113,645 A | 9/1978 | Santora |
| 4,548,821 A | 10/1985 | Hall et al. |
| 4,740,366 A | 4/1988 | Winston et al. |
| 5,089,162 A | 2/1992 | Rapisarda et al. |
| 5,260,053 A | 11/1993 | Chappell et al. |
| 5,554,588 A | 9/1996 | Behan et al. |
| 5,698,253 A | 12/1997 | Dekker et al. |
| 5,837,671 A | 11/1998 | Kaiser |
| 5,874,070 A | 2/1999 | Trinh et al. |
| 5,919,440 A | 7/1999 | Kaiser et al. |
| 5,942,217 A | 8/1999 | Woo et al. |
| 5,990,076 A | 11/1999 | Gaudin et al. |
| 6,025,186 A | 2/2000 | Kirk et al. |
| 6,031,147 A | 2/2000 | Gross |
| 6,727,221 B1 | 4/2004 | Wilson et al. |
| 6,753,308 B1 | 6/2004 | Richardson et al. |
| 7,585,833 B2 | 9/2009 | Fadel et al. |
| 8,821,847 B2 | 9/2014 | Perring et al. |
| 2002/0192174 A1 | 12/2002 | Kawakami et al. |
| 2003/0072733 A1 | 4/2003 | McGee et al. |
| 2003/0180238 A1 | 9/2003 | Sakurai et al. |
| 2004/0266302 A1 | 12/2004 | DiSalvo et al. |
| 2005/0154133 A1 | 7/2005 | Engelhardt et al. |
| 2009/0257974 A1 | 10/2009 | Evans et al. |
| 2013/0039876 A1 | 2/2013 | Perring et al. |
| 2013/0039877 A1 | 2/2013 | Perring et al. |

FOREIGN PATENT DOCUMENTS

| | | |
|---|---|---|
| DE | 4411664 A1 | 10/1995 |
| EP | 0480520 A1 | 4/1992 |
| EP | 0509409 A1 | 10/1992 |
| EP | 0731160 A2 | 9/1996 |
| EP | 0890355 A1 | 1/1999 |
| EP | 0965326 A | 12/1999 |

(Continued)

OTHER PUBLICATIONS

XP002461159; Database WPI Week 200377, Derwnt Publications Ltd. London, GB; AN 2003-818322 dated Dec. 14, 2007.

(Continued)

*Primary Examiner* — Mina Haghighatian

(74) *Attorney, Agent, or Firm* — Norris McLaughlin, PA

(57) ABSTRACT

Perfume compositions comprise between 10% and 30% in total weight of perfume ingredients selected from two groups, Group A, Group B, with the provisos that over 5% but less than 15% of the perfume composition must comprise Group A ingredients, and for compositions comprising less than 10% of Group A ingredients in the aggregate percentage of Group B ingredients present must be at least equal to the expression (2*/10−A %) where A % is the total percentage of Group A ingredients in the composition.

17 Claims, No Drawings

(56) References Cited

FOREIGN PATENT DOCUMENTS

| | | |
|---|---|---|
| EP | 1116788 A | 7/2001 |
| EP | 1133982 A2 | 9/2001 |
| EP | 1321508 A | 6/2003 |
| JP | 2003147386 A | 5/2003 |
| WO | 8900042 A1 | 1/1989 |
| WO | 9425077 A1 | 11/1994 |
| WO | 9612467 A1 | 5/1996 |
| WO | 9630470 A1 | 10/1996 |
| WO | 9746187 A1 | 12/1997 |
| WO | 9825562 A1 | 6/1998 |
| WO | 9826808 A1 | 6/1998 |
| WO | 9850011 A1 | 11/1998 |
| WO | 9856889 A | 12/1998 |
| WO | 9906078 A1 | 2/1999 |
| WO | 0001356 A1 | 1/2000 |
| WO | 0037117 A1 | 6/2000 |
| WO | 0051652 A1 | 9/2000 |
| WO | 0143784 A2 | 6/2001 |
| WO | 0181915 A1 | 11/2001 |
| WO | 0193814 A | 12/2001 |
| WO | 0247472 A1 | 6/2002 |
| WO | 0249600 A | 6/2002 |
| WO | 03051410 A1 | 6/2003 |
| WO | 03051413 A1 | 6/2003 |
| WO | 03088933 A | 10/2003 |
| WO | 2004008051 A1 | 1/2004 |
| WO | 2004009749 A | 1/2004 |
| WO | 2004010325 A1 | 1/2004 |
| WO | 2004098667 A | 11/2004 |
| WO | 2004108177 A1 | 12/2004 |
| WO | 2005044320 A1 | 5/2005 |
| WO | 2005110499 A1 | 11/2005 |
| WO | 2006095200 A | 9/2006 |

OTHER PUBLICATIONS

English Language Abstract for JP2003147386.
International Search report for PCT/GB2007/002980 dated Dec. 20, 2007.
Written Opinion of the International Searching Authority dated Dec. 20, 2007.

PERFUME COMPOSITIONS

This is a Divisional patent application of U.S. Ser. No. 13/651,958 filed on 15 Oct. 2012, which in turn is a Divisional patent application of U.S. Ser. No. 12/375,756 filed on 18 Feb. 2009, which in turn was filed under 35 USC 371 based on PCT/GB2007/002980, and which claims priority to GB 0615583.2 filed 5 Aug. 2006.

FIELD OF THE INVENTION

This invention relates to perfume compositions, to consumer products containing such perfume compositions, and to the use of such perfume compositions to provide deodourant effects including in particular inhibiting and ameliorating the odour of urine. The invention is particularly concerned with perfume compositions that inhibit the bacterial generation of ammonia from urea.

BACKGROUND TO THE INVENTION

The unpleasantness of urine malodour is an age-old problem. When urine is excreted into absorbent articles such as clothing, diapers or incontinence pads, or onto floors surrounding urinals or WC bowls, an ammoniacal malodour may often be detected within a short time. The same problem occurs in pet litter, and may of course be relevant anywhere in the house for households including cats or dogs, etc.

Urine is a clear, transparent fluid that normally has an amber color, and when fresh is generally of low odour. The average amount of urine excreted by a human in 24 hours is about 1,200 cubic centimeters. Chemically, urine is mainly an aqueous solution of sodium chloride and organic substances such as urea and uric acid. Normally, it contains about 960 parts of water to 40 parts of solid matter. Many hundreds of different mineral salts and organic compounds are present in urine, albeit at trace levels for a significant proportion of these. The pH of normal urine is between 4.5 and 7.8, but usually it ranges between 5.0 and 6.0, due to obligatory excretion of acid produced every day.

The major components of urine malodour are: ammonia, volatile fatty acids (primarily acetic, propionic, butyric, formic); volatile sulphur compounds e.g. hydrogen sulfide ($H_2S$) and methyl sulphides such as methyl mercaptan ($CH_3SH$); other nitrogenous compounds such as indole, skatole, pyridine, pyrrole, ethylamine; various other volatiles including benzyl alcohol, phenol, p-cresol, ethanol, methanol, acetone, methyl ethyl ketone, acetaldehyde, propionaldehyde, pentanone, heptanone, propanol, butanol, octanol. These odourous molecules are mainly produced as a result of the bacterial degradation of exogenous materials such as urea and uric acid found in urine, though trace levels of certain materials may reflect materials found in the diet or in the environment. The nitrogenous bases, in particular ammonia, contribute significantly to the malodour recognised by most people from used diapers or other hygiene products such as adult incontinence products. This malodour arises at least partly from the bacterially mediated degradation of urea, from the metabolism of microorganisms present on the skin or from the urogenital tract, for example from the growth of *Proteus* and *Micrococcus* species. All strains of *Proteus* spp. form the enzyme urease during their metabolism. Urease has the ability to rapidly break down urea (constituting about 2% of human urine) into ammonia causing unpleasant odour. The headspace composition above stale urine comprises a variety of materials, but the dominant malodour contributor under most conditions is invariably ammonia. Techniques that lead to reduction in the amount of ammonia present above urine are therefore of possible utility in product sectors associated with sanitation, hygiene, and incontinence. Several approaches are known in the art that address this need.

Antimicrobial agents used in personal products are designed to reduce the population, inhibit the growth or diminish the metabolic activities of microorganisms associated closely with the body-on the surface of the skin, in mucosal surfaces, in the urogenital tract, etc. Typical agents of this nature include triclosan (2',4,4'-trichloro-2-hydroxydiphenyl ether) and zinc oxide which are well known to exert antimicrobial and deodourant effects. The use of common deodourant actives results in a non-selective antimicrobial action exerted upon most of the skin's natural microflora. This can represent an undesirable feature of such deodourant formulations, since the natural microflora provides a protective barrier (colonisation resistance) against invasion by potentially pathogenic bacteria. Certain perfume components and mixtures thereof may contribute to such antimicrobial effects. For example, published US application US2004266302 relates to a disposable absorbent article containing an encapsulated antimicrobial essential oil for odour control.

PCT publication WO 2002/47472 relates to products and methods that utilise a urease inhibitor formed from a polyanionic, and preferably amine-based, chelating agent and a divalent heavy metal ion, to prevent or minimize ammonia odour produced by the degradation of urea in secreted or excreted body fluids. Similarly WO 97/46187 relates to absorbent articles in particular sanitary napkins and panty liners having an odour control system comprising a polyfunctionally substituted aromatic chelating agent for improved odour control.

Much of the art is concerned with the use of odour absorbent materials. For example, WO 2001/80915 relates to absorbent articles that comprise a cationic polysaccharide, preferably chitosan material, and silicate. These articles claim to deliver improved odour control performance (synergistic odour reduction) and improved fluid handling properties/absorption performance. WO 94/25077 relates to odour control through an absorbent article containing a boric acid/sodium tetraborate buffer. EP 509409 relates to malodour control though the design of an absorbent article containing a deodourizing blend of anhydrous, non-buffer blend of at least basic and pH neutral odour absorbing particles. U.S. Pat. No. 6,031,147 discloses an absorbent product comprising a hydrogel-forming polymeric absorbent material and a surface-active agent such as ethoxylated sorbitan monooleate, having a hydrophilic/lipophilic balance of less than about 12.

WO 99/06078 describes absorbent materials containing cyclodextrin as an odour control material. WO 98/26808 describes odour control provided by a combination of a material that inhibits the formation of odour (and has at least one attribute selected from the group consisting of antimicrobial activity, urease inhibition activity, pH adjustment activity) and an odour-absorbing material for objectionable odour molecules selected from the group consisting of cyclodextrin, zeolite, activated carbon, kieselguhr, acid salt forming materials and mixtures thereof. The scent signal is provided by cyclodextrin/perfume inclusion complexes and/or matrix perfume microcapsules to assure the wearer that the product is working.

WO 2000/51652 describes the use of oxidising agents such as a peroxyacid in combination with an odour-absorbing agent such as silica and/or zeolite. WO2003/051413 and WO 2003/051410 relate to a fibrous absorbent material or cellulose fibers treated with a carboxylic acid based odour control agent.

Perfumes have long been recognised as beneficial in hygiene and sanitary sectors. WO 98/25562 describes a diaper design that contains perfume zones and microcapsules as release agents to provide odour control. Published application US 2003/072733 describes a process for absorbing moisture and/or malodour while providing a fragrance to the surrounding ambience. WO 2005/044320 relates to a dual purpose volatile substance controlling composition comprising a sorbent and a fragrance component designed to control malodours including those resulting from bodily fluids. The design involves volatile substance sorption directly linked to fragrance release.

Perfumes may simply mask malodours. WO 2004/10325 describes sanitary absorbent articles comprising a non-aqueous volatile cooling agent such as menthyl lactate or perfume. WO 2004/108177 describes the incorporation of a starch-encapsulated accord into products that releases perfume to minimise odour. However, perfume compositions have been disclosed which exhibit effective deodourant action for specific malodours. For example, WO 2000/01356 describes certain perfume components and compositions thereof, useful in reducing or preventing body malodour. The perfume components (or compositions comprising the perfume components) are described as inhibiting coryneform bacteria that are capable of catabolising fatty acids and are responsible for the production of short chain fatty acid malodour. In this way, the perfume components (or compositions thereof) in-use produce a deodourant effect. However, many of the deodourant perfumes disclosed in the art have relatively high odour intensities that are unsuitable for use in the sanitary or incontinence product sector, and/or are not effective in counteracting or inhibiting ammonia malodour.

In spite of the above mentioned disclosures there still exists a need for cost-effective products that combat urine-derived malodour more efficiently, both from the perspective of malodour prevention as well as malodour amelioration, and do not suffer from the potential disadvantages of exploiting highly antimicrobial actives, whilst benefiting from the presence of perfumes that enjoy broad consumer acceptability.

It has now been surprisingly found that particular perfume compositions are capable of inhibiting the development of ammonia from urea at sub-minimum inhibitory growth concentrations (MIC), and are effective in counteracting urine malodour in spite of exhibiting relatively low perfume odour intensities.

SUMMARY OF THE INVENTION

In one aspect, this invention provides a perfume composition that inhibits the formation of urine malodour, and is effective in ameliorating the perception of urine malodour if present. Such a perfume composition comprises between 10% and 30% in total by weight of perfume ingredients selected from two groups:

Group A, consisting of (3Z)-hex-3-enyl acetate; 3-(1,3-benzodioxol-5-yl)-2-methylpropanal; (3Z)-hex-3-en-1-ol; 1-[4-(methyloxy)phenyl]ethanone; 3-methyl-5-phenylpentan-1-ol; 5-heptyldihydrofuran-2(3H)-one; phenylmethyl acetate; 2-(4-methylcyclohex-3-en-1-yl)propan-2-ol; (3E)-4-(2,6,6-trimethylcyclohex-2-en-1-yl)but-3-en-2-one; (3E)-4-(2,6,6-trimethylcyclohex-1-en-1-yl)but-3-en-2-one; 4-hydroxy-3-(methyloxy)benzaldehyde; 1-methyl-3-(2-methylpropyl)cyclohexanol; 7,9-dimethylspiro[5.5]undecan-3-one; perfume 1 being LAVANDIN AB8381; methyl 2,4-dihydroxy-3,6-dimethylbenzoate; 3,7-dimethyl-octan-1-ol; 2-(methyloxy)-4-propylphenol; perfume 2 being ROSENTA AB8428; 1-{[(1R,2S)-2-(1,1-dimethylethyl)cyclohexyl]oxy}butan-2-ol; perfume 3 being HEADSPACE FREESIA AB7254A; 5-hexyldihydrofuran-2(3H)-one; prop-2-enyl[(2-methylbutyl)oxy]acetate; 1,3-benzodioxole-5-carbaldehyde; [4-(1-methylethyl)cyclohexyl]methanol; 2-hexylcyclopent-2-en-1-one; methyl(2E)-3-phenylprop-2-enoate; 2,6-dimethyloct-7-en-2-ol; 2-methyl-3-[4-(1-methylethyl)phenyl]propanal; and Group B consisting of 2-phenylethanol; 3,7-dimethyloctan-3-ol (tetrahydro linalol), 2-(methyloxy)-4-[(1E)-prop-1-enyl]phenyl acetate; 4-(methyloxy); (2E)-1-(2,6,6-trimethylcyclohex-2-en-1-yl)but-2-en-1-one; perfume 4 being BERGAMOT AB8392, (3E)-3-methyl-4-(2,6,6-trimethylcyclohex-2-en-1-yl)but-3-en-2-one; cyclopentadecanone; cyclohexadecanolide; prop-2-enyl 3-cyclohexyipropanoate; 3-[3-(1-methylethyl)phenyl]butanal; (3Z)-hex-3-enyl methyl carbonate (1-methyl-2-{[(1S,3R,5R)-1,2,2-trimethylbicyclo[3.1.0]hex-3-yl] methyl}cyclopropyl)methanol; [3,3-bis(methyloxy)propyl] benzene; perfume 5 being COUMAREX I MOD; tricyclo [5.2.1.0$^{\{2,6\}}$]dec-4-en-8-yl propanoate;

with the provisos that over 5% but less than 15% of the perfume composition must comprise Group A ingredients, and for compositions comprising less than 10% of Group A ingredients the percentage of Group B ingredients present must be at least equal to the expression $2*(10-A\%)$ where A % is the total percentage of Group A ingredients in the composition.

In another aspect, the invention relates to a method of preventing or ameliorating urine malodour comprising bringing into contact with urine or urine residues an effective amount of a perfume composition according to the invention.

At least 0.3 wt % of a perfume ingredient must be present before it may be considered to contribute significantly towards the efficacy of the compositions, i.e. perfume ingredients present at concentrations below 0.3 wt % and ignored in the calculation of the number of Group A and Group B ingredients in the composition.

Preferred perfume compositions comprise at least three Group A ingredients, more preferably at least four ingredients and most preferably at least six ingredients.

For the purposes of this invention a perfume composition is defined as a mixture of perfume ingredients, if desired mixed with or dissolved in a suitable solvent or solvents and/or mixed with a solid substrate. Perfume ingredients are well known to those skilled in the art, and include those mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA. Perfume ingredients may include natural products such as extracts, essential oils, absolutes, resinoids, resins, concretes etc., and also synthetic substances such as hydrocarbons, alcohols, aldehydes, ketones, ethers, acids, esters, acetals, ketals, nitriles, etc., including saturated and unsaturated compounds, aliphatic, macrocyclic and heterocyclic compounds.

References herein to the percentage by weight of perfume ingredients means relative to the total weight of perfume ingredients in the perfume composition and includes materials that are used within perfumery as vehicles or solvents for other perfume ingredients, for example dipropylene glycol, isopropyl myristate, benzyl benzoate, diethyl phthalate, triacetin and triethyl citrate.

Perfumes constructed according to the above design provide effective urease inhibition without being overtly strongly antimicrobial (as indicated by tests described below) and also are able to counteract urine malodour olfactorily.

In a further aspect, the invention provides a perfumed consumer product comprising a perfume composition in accordance with the invention. For the purposes of this invention a consumer product means comprises a solid, liquid or soft solid formulation especially for use in or on a substrate such as skin, hair (including fur), clothing or hard surface. Examples of such consumer products include bathroom and kitchen cleaners, carpet cleaners, polishes, personal body refreshers and deodourants, pet deodourants, in a variety of formats such as liquids (particularly as delivered by trigger sprays or aerosols), gels and powders, all of which are well known in the art. Another example of a consumer product relevant to the present invention is pet litter.

In such consumer products as little as 0.1% by weight of the perfume composition in the product will suffice.

The invention also covers use of a perfume composition according to the invention for the purpose of inhibiting urea breakdown to form ammonia. Preferred features of this aspect are as discussed below in connection with the perfume composition of the invention. A concomitant effect of the inhibition of ammonia production is that pH remains relatively constant, or at least the rate of increase of pH is much lower than in the absence of the perfume composition. Such pH control may be of indirect benefit in areas other than malodour management.

In a further aspect, the invention provides an article suitable for preventing or ameliorating urine malodour, comprising an effective amount of a perfume composition according to the invention.

Such articles of manufacture include diapers, incontinence pads, hygienic body wipes, and catamenials including sanitary pads and sanitary towels. Perfume compositions of the invention may be incorporated into or onto such articles by any suitable means known in the art, for example by bringing them into contact with adsorbents present in such articles, although they be used in association with a wide variety of elements of such articles. It may sometimes be advantageous to encapsulate the perfumes of the invention prior to incorporation into such articles.

Perfume Ingredients of the Invention

Perfumes formulated to the guidelines described herein will maintain the pH of a urea-supplemented microbial suspension (as described below in Example 1) at a pH that is at least 1.2 pH units lower than that of a non-perfumed control. It is believed that this difference in pH is directly correlated to a decrease in ammonia production. It is highly desirable that the effect is achieved at sub-inhibitory growth levels. Two groups of perfume ingredients have been identified. Group A materials have the highest efficacy, but Group B may be used in place of a fraction of the Group A materials where this is desirable in order to achieve the right balance of hedonic properties, anti-microbial action and sensory-derived malodour counteraction.

Group A ingredients are listed below, where names in parentheses represents equivalent names—either trivial names commonly used within the fragrance and flavour industry, or tradenames that are sources for the material cited.

Group A Materials:
(3Z)-hex-3-enyl acetate(cis-3-hexenyl acetate),
3-(1,3-benzodioxol-5-yl)-2-methylpropanal [HELIONAL (IFF)],
(3Z)-hex-3-en-1-ol(cis-3-hexenol)
1-[4-(methyloxy)phenyl]ethanone(paramethoxy acetophenone),
3-methyl-5-phenylpentan-1-ol [MEFROSOL (G)],
5-heptyldihydrofuran-2(3H)-one (undecalactone gamma),
phenylmethyl acetate(benzyl acetate),
2-(4-methylcyclohex-3-en-1-yl)propan-2-ol(terpineol alpha),
(3E)-4-(2,6,6-trimethylcyclohex-2-en-1-yl)but-3-en-2-one (ionone alpha),
(3E)-4-(2,6,6-trimethylcyclohex-1-en-1-yl)but-3-en-2-one (ionone beta).
4-hydroxy-3-(methyloxy)benzaldehyde (vanillin),
1-methyl-3-(2-methylpropyl)cyclohexanol [ROSSITOI, (G)],
7,9-dimethylspiro[5,5]undecan-3-one [DISPIRONE (G)],
perfume 1 being LAVANDIN AB8381,
methyl2,4-dihydroxy-3,6-dimethylbenzoate (moss oakmnoss synthetic),
3,7-dimethyloctan-1-ol(tetrahydrogeraniol),
2-(methyloxy)-4-propylphenol(dihydroeugenol),
perfume 2 being ROSENTA AB8428,
1-{[(1R,2S)-2-(1,1-dimethylethyl)cyclohexyl]oxy}butan-2-ol [AMBER CORE (G)],
perfume 3 being HEADSPACE FREESIA AB7254A,
5-hexyldihydrofuran-2(3H)-one (decalactone gamma),
prop-2-enyl[(2-methylbutyl)oxyacetate(Allyl amyl glycolate),
1,3-benzodioxole-5-carbaldehyde (heliotropin),
[4-(1-methylethyl)cyclohexyl]methanol [MAYOL (F)].
2-hexylcyclopent-2-en-1-one(iso-jasmone),
methyl(2E)-3-phenylprop-2-enoate(methyl cinnamate),
2,6-dimethyloct-7-en-2-ol(dihydromyrcenol).
2-methyl-3-[4-(1-methylethyl)phenyl]propanal(cyclamen aldehyde).

Group B Ingredients:
2-phenylethanol(phenyl ethyl alcohol);
3,7-dimethyloctan-3-ol(tetrahydrolinalool);
2-(methyloxy)-4-[(1E)-prop-1-enyl]phenyl acetate (isoeugenyl acetate);
4-(methyloxy)benzaldehyde(anisic aldehyde);
(2E)-1-(2,6,6-trimethylcyclohex-2-en-1-yl)but-2-en-1-one(damascene alpha);
perfume 4 being BERGAMOT AB8392;
(3E)-3-methyl-4-(2,6,6-trimethylcyclohex-2-en-1-yl)but-3-en-2-one(methyl ionone alpha iso);
Cyclopentadecanone [SILVANONE (G)];
Oxacycloheptadecan-2-one (SILVANONE (G), cyclohexadecanolide);
prop-2-enyl3-cyclohexylpropanoate(allyl cyclo hexyl propionate);
3-[3-(I-methylethyl)phenyl]butanal [FLOROHYDRAL (G)];
(3Z)-hex-3-enyl methyl carbonate(cis-3-hexenyl methyl carbonate);
(1-methyl-2-{[(1S,3R,5R)-1,2,2-trimethylbicyclo[3.1.0]hex-3-yl]methyl}cyclopropyl)methanol [JAVANOL (G)];
[3,3-bis(methyloxy)propyl]benzene(dimethyl hydro cinnamyl);
perfume 5 being COUJMAREX I MOD (IFF);
tricyclo[5.2.1.0$^{\{2,6\}}$]dec-4-en-8-yl propanoate [FLOROCYDENE (G)].

Key:
G=Givaudan;
IFF=International Flavours and Fragrances;
F=Firmenich
wherein perfumes 1 to 5 have the following compositions:

| Ingredient | Perfume 1 | Perfume 2 | Perfume 3 | Perfume 4 | Perfume 5 |
|---|---|---|---|---|---|
| Allylamyl glycolate | 0.8 | | | | |
| Anisaldehyde | | | | | 0.3 |
| Benzophenone | | 2.0 | | | |
| Borneol | 1.0 | | | | |
| Camphene | 0.8 | | | | |
| Camphor | 9.2 | | | | |
| Caryophyllene | 4.5 | | | | |
| Cedarwood Texan oil | 0.8 | | | | |
| Cineole | 7.0 | | | | |
| Citral Diethylacetal | | | 1.5 | | |
| Citronellyl formate | | 1.8 | | | |
| Citronellyl propionate | 2.5 | | | | |
| Dihydrolinalol | 6.5 | | | | |
| Dihydro myrcenyl acetate | | | | 11.0 | |
| Dihydro Terpinyl Acetate | 13.5 | | | 31.5 | |
| 2,6-Dimethylheptan-2-ol | 2.0 | | | | |
| Dipropylene glycol | | 5.0 | | | 88.0 |
| Geranylacetate | | 5.0 | | | |
| Geranylacetone | | 1.0 | | | |
| Geranyl formate | | 1.2 | | | |
| HERCOLYN DE | | 4.5 | | | |
| gamma-hexalone | | | | | 5.6 |
| beta-ionone | | 3.0 | 24.5 | | |
| Linalyl acetate | | 1.0 | | 32.0 | |
| MEFROSOL | 10.0 | 14.0 | | | |
| 3-Methylbut-2-enyl benzoate | | | | | 4.5 |
| Neryl acetate | | | | 1.0 | |
| Ocimene | | 1.0 | | | |
| para-tert-butylcyclohexyl acetate | 4.5 | | | | |
| Phenyl acetaldehyde dimethylacetal | | 2.0 | | | |
| 2-phenylethyl alcohol | | 27.0 | | | |
| 2-phenylethyl phenylacetate | | 24.0 | | | |
| 2-phenylethyl salicylate | | 1.0 | | | |
| alpha-pinene | | | | 1.4 | |
| beta-pinene | | | | 6.8 | |
| Clary sage oil | | 0.8 | | | |
| gamma-terpinene | | | | 6.0 | |
| alpha-terpineol | 4.2 | | 12.2 | | |
| Terpinyl acetate | 17.9 | | | | |
| alpha-terpinyl isobutyrate | 2.5 | | | | |
| Tetrahydrogeraniol | | 1.4 | | | |
| Tetrahydrolinalol | | | 60.3 | 4.0 | |
| Tetrahydrolinalyl acetate | 4.5 | | | | |
| Minor components | 6.8 | 5.3 | 3.0 | 4.8 | 1.6 |
| Totals | 100 | 100 | 100 | 100 | 100 |

Key
MEFROSOL is 3-methyl-5-phenylpentan-1-ol
HERCOLYN DE is a mixture of methyl dihydroabietate and tetrahydroabietate
Particularly preferred Group A materials are:
(3Z)-hex-3-enyl acetate; 3-(1,3-benzodioxol-5-yl)-2-methylpropanal; (3Z)-hex-3-en-1-ol; 3-methyl-5-phenylpentan-1-ol; 5-heptyldihydrofuran-2(3H)-one; phenylmethyl acetate; 2-(4-methylcyclohex-3-en-1-yl)propan-2-ol; 2,6-dimethyloct-7-en-2-ol; (3E)-4-(2,6,6-trimethylcyclohex-2-en-1-yl)but-3-en-2-one; (3E)-4-(2,6,6-trimethylcyclohex-1-en-1-yl)but-3-en-2-one; 4-hydroxy-3-(methyloxy)benzaldehyde; 1,3-benzodioxole-S-carbaldehyde.

It has also been discovered that the presence of different perfume solvents within the composition may affect activity slightly. Embodiments incorporating triethyl citrate are preferred.

EXAMPLES

Example 1 MIC Estimation for Fragrance and Fragrance Ingredients

The minimum inhibitory concentration of perfumes may be determined by the following method.

Stock solutions (8% w/w) of perfume were prepared in sterile tryptone soya broth.

Test Strain:

*Proteus vulgaris* NCTC 4175 (National Collection of Type Cultures, Public Health Laboratory Service, Central Public Health Laboratory, 61 Colindale Avenue, London)

Cultures were grown in 10 ml of tryptone soya broth (TSB) (Oxoid, Basingstoke, UK), for 16-24 hours, in shaken flasks at 37° C. The cultures were then diluted in sterile 0.1% special peptone solution (Oxoid, Basingstoke, UK) to give a concentration of bacteria of approximately $10^6$ colony-forming units (cfu) per ml.

Test ingredients were diluted in sterile TSB. For each test bacterial culture, each row of a standard, 96-well plastic microtitre plate (labelled A-H) was allocated to one sample, thus eight samples per plate. Row H contained only TSB for use as a bacterial control to indicate the degree of turbidity resulting from bacterial growth in the absence of any test material. Aseptically, 200 μl of the initial dilution of ingredient was transferred to the 1st and 7th well of the appropriate row. All other test wells were filled with 100 μl of sterile TSB using an 8-channel micropipette. The contents of each of the wells in column 1 were mixed by sucking samples up and down in pipette tips, before 1001 μl was transferred to column 2. The same sterile pipette tips were used to transfer 100 μl of each well in column 7, into the appropriate well in column 8. This set of eight tips was then discarded into disinfectant solution. Using eight fresh, sterile tips the process was repeated by transferring 100 μl from column 2 into column 3 (and 8 into 9). The process was continued until all wells in columns 6 and 12 contained 200 μl. After mixing, 100 μl was discarded from wells in columns 6 and 12 to waste. Finally, 100 μl of pre-diluted bacterial culture (approx. $10^6$ cfu/ml) was added, thus giving 200 μl final volume in each well.

A blank plate was prepared for each set of eight samples in exactly the same way, except that 100 μl of sterile 0.1% special peptone was added instead of bacterial culture. Test and control plates were sealed using autoclave tape and incubated for 18 hours at 37° C.

The microtitre plate reader (Thermo Multiskan Ascent) was preset to gently agitate the plates, to mix the contents. The absorbance at 540 nm was used as a measure of turbidity resulting from bacterial growth. Both control (uninoculated plate) and inoculated plates were read for each set of samples. The absorbance readings from the control plate were subtracted from the relevant inoculated plate readings thus removing turbidity due to perfume and possible colour changes during incubation. Thus the corrected readings generated were absorbances resulting from turbidity from bacterial growth. The MIC was taken as the concentration of ingredient required to inhibit growth so that the average change in absorbance during the incubation period was <0.3.

Example 2 Urease Assay—Estimation of Fragrance and Fragrance Ingredients Effect on Ammonia Production The method adopted was based on the rapid method devised by C. A. Stuart, Elizabeth van Stratum and Robert Rustigan Further Studies on Urease Production by *Proteus* and Related Organisms J. Bacteriol. 1945, 49: 437-444.

SSR Medium: 380 ml distilled water, 364 mg $KH_2PO_4$, 380 mg $Na_2HPO_4$, 8 g Urea, 40 mg Yeast extract, 20 ml 0.02% phenol red indicator, pH 6.8, solution filter sterilised.

Culture: Liquid culture of *P. vulgaris* NCTC4175 was prepared by adding loops of fresh culture from solid media (Tryptone Soya Agar) to sterile 0.1% special peptone solution. Absorbance of culture was adjusted to be OD610 nm >2.3

Fragrances were aseptically prepared at 2500 ppm in medium in duplicate (5 ml volumes) using solubiliser Synperonic 91/10 at ratio of 1:2 fragrance: solubiliser. In addition 5 ml volumes of positive and negative controls were prepared. Positive controls and all test solutions were inoculated by adding 2001 µl of prepared culture, mixed and incubated for 24 hours @ 37° C. No culture was added to the negative growth controls. Initially solutions were orange in colour. Urease activity can be noted by the production of a purple/red colour, indicating high pH resulting from ammonia production. The degree of urease activity/ammonia production was assessed by pH electrode.

Example 3 Perfume Compositions

Fragrance formulations 3.2, 3.4, and 3.8 detailed in Table 1 were created following the creative guidelines of the present invention. Formulations, 3.1, 3.3, 3.5, 3.6 and 3.7 are comparatives that fall outside these guidelines. All examples bar numbers 3.5 and 3.6 meet the Urease Inhibition Assay target of a difference of 1.2 pH units compared to the positive control. However only Formulations 3.2, 3.4 and 3.8 achieve this effect at sub-MIC level. These three perfumes were also evaluated in a urine malodour test as described in example 3 of PCT/GB2007/00 1172 using malodour model A of example 1 therein. All three were found to be effective in reducing the perception of the urine malodour.

TABLE 1

Perfume Formulations (% w/w)

| Ingredient | 3.1 | 3.2 | 3.3 | 3.4 | 3.5 | 3.6 | 3.7 | 3.8 |
| --- | --- | --- | --- | --- | --- | --- | --- | --- |
| Acetyl tributyl citrate | 10 | 10 | | 5 | | 5 | | |
| Allyl amyl glycolate (A) | | | 1 | | | | 3 | |
| Amyl salicylate | 5 | 5 | | | 4 | 7 | | |
| Anisic aldehyde (B) | | 5 | 4 | 0.5 | | | | |
| BANGALOL (G) | | | | | 0.3 | 0.3 | | |
| Benzyl acetate (A) | | 1 | | | | | | |
| cis-3-hexenol (A) | 0.5 | | 0.5 | | | | | |
| cis-3-hexenyl salicylate | | | | | 1 | | | |
| COUMAREX I MOD (B) | | 5 | | | | | | |
| Cyclamen aldehyde (A) | | | | | | | 5 | |
| Decalactone gamma (A) | | | | | | | 0.5 | |
| Dihydromyrcenol (A) | 10 | | 5 | | | | | |
| DISPIRONE (G) (A) | | 0.1 | 0.5 | | | | | |
| Ethylene brassylate | 10 | 15 | | 10 | 14.5 | 12 | | 12 |
| ETHYL SAFRANATE (G) | | | | | | 0.2 | | |
| FLOROSA (G) | | | | | 0.2 | 0.5 | | |
| HABANOLIDE (F) | | 1 | | | 2 | 3 | | |
| HELIONAL (A) | 1 | | 1 | | 1 | | 1 | 2 |
| Heliotropin (A) | 3 | | | 1 | 1 | | | 2 |
| Hexyl salicylate | 5 | | | 12 | 10 | 12 | 10 | 15 |
| Ionone alpha (A) | | | | | 2 | | | |
| MAYOL (F) (A) | | | 1 | | | | | |
| MEFROSO (G) (A) | 0.9 | 1 | | 1 | 1 | | | 2.5 |
| Methyl dihydrojasmonate | | 8 | 14 | 15 | | 15 | 10 | 8 |
| para tert butyl cyclo hexyl acetate | | | | 5 | | | | |
| Moss oakmoss synthetic (A) | 0.1 | | | | | | | |
| Phenoxyethanol | | | 5 | 10 | | | | 5 |
| Phenyl ethyl alcohol (B) | 10 | 7.5 | 5 | 6.5 | 7 | | 10 | |
| ROSSITOL (G) (A) | 2 | | | | | | | |
| SILVANONE (G) (B) | 1 | | | | | | | |
| Terpineol alpha (A) | | | | 6 | | | 5 | 2 |
| Tetrahydrogeraniol (A) | | 1.5 | | 3 | | | | |
| Tetrahydrolinalol (B) | 5 | 2 | 1 | 1 | 3 | | 10.5 | |
| Triethyl citrate | 34 | 36 | 50 | 33 | 48 | 50 | 45 | 50 |
| Undecalactone gamma (A) | 0.5 | | | | | | | 0.5 |
| Vanillin (A) | 2 | 1.9 | | | 2 | | | 1 |
| Total Group A ingredients | 20 | 5.5 | 15 | 7 | 5 | 0 | 14.5 | 10 |
| Total Group B ingredients | 16 | 19.5 | 10 | 8 | 10 | 0 | 20.5 | 0 |
| Total Group A + Group B | 36 | 25 | 25 | 15 | 15 | 0 | 35 | 10 |

KEY:
(A) = Group A material;
(B) = Group B material
(G) = Givaudan;
(F) = Firmenich Following the methods outlined previously, the above examples give results detailed in Table 2.

TABLE 2

Results of MIC and Urease inhibition assays

| Fragrance | Urease Inhibition Assay Results at 2500 ppm | | MIC assay MIC vs *Pr. vulgaris* (ppm) |
|---|---|---|---|
| | Average pH | pH unit difference from +ve control | |
| Example 3.1 | 7.50 | 1.60 | 2500 |
| Example 3.2 | 7.85 | 1.25 | 5000 |
| Example 3.3 | 7.69 | 1.41 | 1250 |
| Example 3.4 | 7.67 | 1.43 | 10000 |
| Example 3.5 | 8.44 | 0.66 | 10000 |
| Example 3.6 | 8.78 | 0.32 | 10000 |
| Example 3.7 | 7.64 | 1.46 | 2500 |
| Example 3.8 | 7.58 | 1.52 | 5000 |
| +ve control | 9.10 | N/A | N/A |
| −ve control | 6.99 | N/A | N/A |

The invention claimed is:

1. A perfume composition which comprises in total, between 10% wt.-30% wt. of perfume ingredients selected from Group A and Group B, wherein:
   two groups:
   Group A consists of:
   3-(1,3-benzodioxol-5-yl)-2-methylpropanal;
   3-methyl-5-phenylpentan-1-ol;
   5-heptyldihydrofuran-2(3H)-one;
   phenylmethyl acetate;
   2-(4-methylcyclohex-3-en-1-yl)propan-2-ol;
   (3E)-4-(2,6,6-trimethylcyclohex-2-en-1-yl) but-3-en-2-one;
   4-hydroxy-3-(methyloxy) benzaldehyde;
   7,9-dimethylspiro[5.5]undecan-3-one;
   3,7-dimethyloctan-1-ol;
   1,3-benzodioxole-5-carbaldehyde;
   or mixtures thereof;
   and,
   Group B consists of:
   2-phenylethanol;
   3,7-dimethyloctan-3-ol (tetrahydro linalol);
   4-(methyloxy)benzaldehyde;
   or mixtures thereof;
   with the provisos that:
   (a) over 5% wt. but less than 15% wt. of the perfume composition must comprise Group A perfume ingredients, and
   (b) in compositions comprising less than 10% wt. of Group A perfume ingredients, the aggregate percentage of Group B perfume ingredients present must be at least equal to the expression 2*(10−A % wt.) where A % wt. is the total percentage of Group A perfume ingredients in the composition.

2. A perfume composition according to claim 1, wherein the Group B perfume ingredient or mixture of Group B perfume ingredients are combined with a mixture of at least three Group A perfume ingredients.

3. A consumer product comprising a solid, liquid or soft solid formulation, which comprises a perfume composition according to claim 2.

4. A perfume composition according to claim 2 wherein the Group B perfume ingredient or mixture of Group B perfume ingredients are combined with a mixture of at least four Group A perfume ingredients.

5. A consumer product comprising a solid, liquid or soft solid formulation, which comprises a perfume composition according to claim 4.

6. A perfume composition according to claim 4 wherein the Group B perfume ingredient or mixture of Group B perfume ingredients are combined with a mixture of at least six Group A perfume ingredients.

7. A consumer product comprising a solid, liquid or soft solid formulation, which comprises a perfume composition according to claim 6.

8. A perfume composition according to claim 1, wherein the Group A perfume ingredients are selected from the group consisting of:
   3-(1,3-benzodioxol-5yl)-2-methylpropanal;
   3-methyl-5-phenylpentan-1-ol;
   5-heptyldihydrofuran-2(3H)-one;
   phenylmethyl acetate;
   2-(4-methylcyclohex-3 en-1-yl)propan-2-ol;
   (3E)-4-(2,6,6-trimethylcyclohex-2-en-1-yl)but-3-en-2-one;
   4-hydroxy-3-(methyloxy) benzaldehyde;
   1,3-benzodioxole-5-carbaldehyde;
   or mixtures thereof.

9. A consumer product comprising a solid, liquid or soft solid formulation, which comprises a perfume composition according to claim 8.

10. A consumer product according to claim 9 which is a catamenial article.

11. A consumer product according to claim 9 which is an incontinence control article.

12. A perfume composition according to claim 1, wherein the perfume composition is effective in inhibiting the formation of ammonium from urea at sub-MIC (minimum inhibitory concentration) concentrations.

13. A consumer product comprising a solid, liquid or soft solid formulation, which comprises a perfume composition according to claim 1.

14. A consumer product according to claim 13 which is a catamenial article.

15. A consumer product according to claim 13 which is an incontinence control article.

16. A method of inhibiting the formation of ammonium from urea, the method comprising the step of:
   contacting urea with a perfume composition according to claim 1.

17. A method of inhibiting the formation of ammonia from urine, the method comprising the step of:
   providing a consumer product which comprises a solid, liquid or soft solid formulation and a perfume composition of claim 1,
   wherein the formation of ammonia from urine is inhibited when urine contacts the perfume composition.

* * * * *